United States Patent [19]

Röchling

[11] Patent Number: 5,354,739

[45] Date of Patent: Oct. 11, 1994

[54] HIGHLY CONCENTRATED EMULSIFIABLE CONCENTRATES OF NEOPHANES AND AZANEOPHANES FOR USE IN PLANT PROTECTION

[75] Inventor: Hans Röchling, Bad Soden im Taunus, Fed. Rep. of Germany

[73] Assignee: Hoechst Aktiengesellschaft, Frankfurt am Main, Fed. Rep. of Germany

[21] Appl. No.: 956,800

[22] Filed: Oct. 5, 1992

Related U.S. Application Data

[63] Continuation of Ser. No. 656,290, Feb. 15, 1991, abandoned.

[30] Foreign Application Priority Data

Feb. 17, 1990 [DE] Fed. Rep. of Germany ....... 4005153

[51] Int. Cl.$^5$ ............................................ A01N 55/02
[52] U.S. Cl. ...................................... 514/63; 514/274; 514/277; 514/332; 514/335; 514/345; 514/348; 514/712; 514/718; 514/720; 514/721
[58] Field of Search .............. 556/445, 447, 448, 454, 556/489; 514/63

[56] References Cited

U.S. PATENT DOCUMENTS

| | | | |
|---|---|---|---|
| 4,775,664 | 10/1988 | Schubert et al. | 514/63 |
| 4,804,653 | 2/1988 | Strunk et al. | 514/63 |
| 4,864,027 | 9/1989 | Shubert et al. | 546/14 |
| 4,883,789 | 11/1989 | Sieburth | 514/63 |
| 4,966,902 | 10/1990 | Schubert et al. | 514/277 |

FOREIGN PATENT DOCUMENTS

| | | |
|---|---|---|
| 0202893 | 11/1986 | European Pat. Off. . |
| 0288810 | 11/1986 | European Pat. Off. . |
| 0224024 | 6/1987 | European Pat. Off. . |
| 0249015 | 12/1987 | European Pat. Off. . |
| 0302701 | 2/1988 | European Pat. Off. . |
| 0336199 | 10/1989 | European Pat. Off. . |
| 3604781 | 2/1986 | Fed. Rep. of Germany . |

0108885 5/1987 Japan .

OTHER PUBLICATIONS

European Search Report EP 91 10 1928.

*Primary Examiner*—Richard L. Raymond
*Assistant Examiner*—Brian M. Burn
*Attorney, Agent, or Firm*—Curtis Morris & Safford

[57] ABSTRACT

Highly concentrated emulsifiable concentrates of neophanes and azaneophanes for use in plant protection Highly concentrated emulsifiable concentrates of compounds of the general formula I

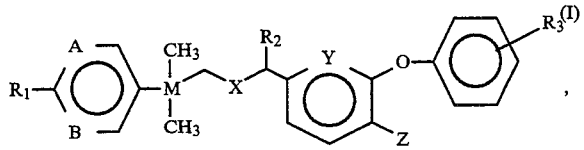

in which A, B = independently of one another CH, $CR_4$ or N,
X = $CH_2$, O or S,
Y = CH or N,
Z = H or F,
$R_1$ and $R_4$ = independently of one another H, halogen, $(C_1-C_3)$-alkyl, $(C_1-C_3)$-halogenoalkyl, $(C_1-C_3)$-alkoxy, $(C_1-C_3)$-halogenoalkoxy, $(C_1-C_4)$-alkylthio or $(C_1-C_4)$-halogenoalkylthio, or $R_1$ and $R_4$ together = —$CH_2$—O—$CH_2$—;
$R_2$ = H, $(C_1-C_3)$-alkyl, ethynyl, vinyl, halogen or cyano,
$R_3$ = H, halogen, $(C_1-C_4)$-alkyl or $(C_1-C_3)$-alkoxy and
M = C or Si, which contain a combination of an anionic and a nonionic emulsifier with a $(C_2-C_{16})$-alkanol.

also have, in addition to a very good spontaneous emulsiliability, a very high emulsion stability.

28 Claims, No Drawings

HIGHLY CONCENTRATED EMULSIFIABLE CONCENTRATES OF NEOPHANES AND AZANEOPHANES FOR USE IN PLANT PROTECTION

This application is a continuation of application Ser. No. 07/656,290, filed Feb. 15, 1991 (abandoned).

The present invention relates to highly concentrated emulsifiable concentrates of compounds of the formula I

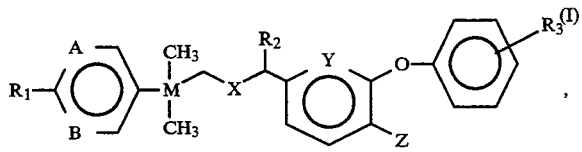

in which

A, B = independently of one another CH, $CR_4$ or N,
$X = CH_2$, O or S,
Y = CH or N,
Z = H or F,
$R_1$ and $R_4$ = independently of one another H, halogen, $(C_1-C_3)$-alkyl, $(C_1-C_3)$-halogenoalkyl, $(C_1-C_3)$-alkoxy, $(C_1-C_3)$-halogenoalkoxy, $(C_1-C_4)$-alkylthio or $(C_1-C_4)$-halogenoalkylthio, or $R_1$ and $R_4$ together = $-CH_2-O-CH_2-$;
$R_2$ = H, $(C_1-C_3)$-alkyl, ethynyl, vinyl, halogen or cyano,
$R_3$ = H, halogen, $(C_1-C_4)$-alkyl or $(C_1-C_3)$-alkoxy and
M = C or Si, which contain a combination of an anionic and a nonionic emulsifier with a $(C_2-C_{16})$-alkanol.

Alkyl and also alkanol contain either a straight-chain or a branched alkyl radical.

Preferably, A and B = CH or N, $X = CH_2$, $R_1 = (C_1-C_3)$-alkoxy, $R_2 = H$, $R_3 = H$ or F and M = Si.

Of the compounds of the formula I, that in which M = Si, $R_1$ = ethoxy, A and B = CH, $X = CH_2$, $R_2 = H$, Y = CH, Z = F and $R_3 = H$ is particularly preferred (Ia).

Active compounds from the group comprising neophanes and azaneophanes (I) have a good plant tolerance and favorable toxicity toward warm-blooded animals, and are suitable for combating animal pests, in particular insects, arachnids and nematodes, which occur in agriculture, in forests, in the preservation of stored products and materials and in the hygiene sector. They are active against normally sensitive and resistant species as against all or individual stages of development (European Patent A-0,224,024, European Patent A-0,249,015 and European Patent A-0,288,810). The conventional types of formulation for insecticides and acaricides, as well as methods for making the neophanes and azaneophanes (I), are also described in these documents.

Neophanes and azaneophanes can be formulated without major difficulties with a combination of anionic and nonionic emulsifiers using the customary solvents, such as, for example, alkylated benzenes or alkyl naphthalenes to give 10 to 70% strength emulsifiable concentrates which have a good spontaneous emulsifiability in water. However, in the case of higher percent strength, in particular 70 to 85% strength, formulations of the neophanes and azaneophanes (I), which are in the form of viscous oils, it has not been possible to discover concentrates having an adequately spontaneous emulsifiability in water, even using the most diverse solvents and emulsifier combinations.

Thus, using a mixture of Ca phenylsulfonate with ®Emulsogen EL 360 and ®Sapogenat T 200 or of Ca phenylsulfonate with Hoe S 3510 and ®Solvesso 200 (Exxon Chemicals) as the solvent, spontaneously emulsifying concentrates of the neophanes and azaneophanes I can only be prepared if the active compound concentrations are kept within up to 40%.

These same emulsifier/solvent combinations did now show an adequate spontaneous emulsifiability in water when used in higher percent strength, in particular 75 to 85% strength, emulsifiable concentrates. Although a good emulsion stability was to be achieved after intensive mixing (vigorous shaking or prolonged intensive stirring), preparations which are emulsified in water rapidly and without considerable mechanical effort are required in practice and also by international test specifications (CIPAC, WHO and the like).

An increase in the amount of emulsifier mixture or the use of other proven emulsifier combinations or other solvents brought no improvement (Tab. I).

TABLE I

| | | | (Data in % by weight) | | | | |
|---|---|---|---|---|---|---|---|
| Content of compound Ia % | Ca phenyl-sulfonate % 1) | Emulsogen EL % 2) | Sapogenat T 200 % 3) | Hoe S 3510 % 4) | Emulsogen EL 9.5 % 5) | Solvent % | Spontaneous emulsifiability |
| 19.6 | 4.3 | 7.5 | 2.9 | | | 65.7 Solvesso 200 | 1 |
| 19.8 | 4.2 | | | 3.7 | | 72.3 Solvesso 200 | 1–2 |
| 39.0 | 5.6 | | | 6.0 | | 49.4 Solvesso 200 | 1–2 |
| 80.0 | 3.0 | | | 7.0 | | 10.0 Solvesso 200 | 4 |
| 80.0 | 3.3 | | | 7.6 | | 9.1 Solvesso 200 | 4 |
| 80.0 | 3.9 | 2.0 | | 7.0 | | 7.1 Solvesso 200 | 4–5 |
| 80.0 | 3.8 | | | 8.6 | | 7.6 Solvesso 200 | 4 |
| 85.0 | 3.0 | | | 7.0 | | 5.0 Solvesso 200 | 4–5 |
| 80.0 | 3.0 | | | 7.0 | | 10.0 N-methyl-pyrrolidone | 4 |
| 80.0 | 3.3 | | | 7.7 | | 9.0 N-methyl-pyrrolidone | 4 |
| 82.0 | 3.6 | | | 8.4 | | 6.0 N-methyl- | 4–5 |

TABLE I-continued (Data in % by weight)

| Content of compound Ia % | Ca phenyl-sulfonate % 1) | Emulsogen EL % 2) | Sapogenat T 200 % 3) | Hoe S 3510 % 4) | Emulsogen EL 9.5 % 5) | Solvent % | Spontaneous emulsifiability |
|---|---|---|---|---|---|---|---|
| 75.0 | 3.6 | | 8.4 | | | 13.0 N-methyl-pyrrolidone | 4 |
| 80.0 | 3.9 | | 7.0 | | 2.0 | 7.1 N-methyl-pyrrolidone | 4 |
| 85.0 | 3.9 | | 7.0 | | 2.0 | 2.1 N-methyl-pyrrolidone | 4–5 |
| 85.0 | 3.8 | | 8.7 | | | 2.5 N-methyl-pyrrolidone | 4 |
| 80.0 | 3.8 | | 8.7 | | | 7.5 N-methyl pyrrolidone | 4 |
| 80.0 | 3.0 | | 7.0 | | | 10.0 Triacetin | 4–5 |
| 80.0 | 3.8 | | 8.7 | | | 7.5 Triacetin | 4 |
| 85.0 | 3.8 | | 8.7 | | | 2.5 Triacetin | 4–5 |

1) Ca phenylsulfonate, Hoechst AG, calcium salt of an alkylarylsulfonic acid (dodecylbenzenesulfonic acid)
2) ® Emulsogen EL, Hoechst AG, fatty acid polyglycol ester, nonionic (36 mol of ethylene oxide (EO)).
3) ® Sapogenat T 200, Hoechst AC, tributylphenol polyglycol ether containing 20 mol of EO.
4) Hoe S 3510, Hoechst AG, block oxyalkylate, nonionic.
5) ® Emulsogen EL 9.5, Hoechst AG.
The rating figures 1–5 have the following meaning:
1 - very good spontaneous emulsifiability
2 - good spontaneous emulsifiability
3 - adequate spontaneous emulsifiability
4 - moderate to poor spontaneous emulsifiability
5 - inadequate spontaneous emulsifiability Such highly concentrated emulsifiable concentrates would have various ecological and also economic advantages over the customary emulsifiable concentrates having an active compound content of about 10–50%:
high flash point
low solvent content and therefore favorable toxicological properties for the user and the environment and
high profitability, since the despatch and packaging costs are lower for the same amount of active compound.

It has now been found, surprisingly, that if a combination of anionic and nonionic emulsifiers with alcohols as the solvent is used, highly concentrated emulsifiable concentrates of the compounds I, in particular of the compound Ia, which, in addition to having a very good spontaneous emulsifiability, also have a very high emulsion stability, can be obtained.

The formulations according to the invention contain the active compounds of the general formula I to the extent of 60–90% by weight, in particular 70 up to and including 85% by weight.

Anionic emulsifiers which can be used are: salts of dodecylbenzenesulfonic acid, salts of optionally chlorinated ($C_{13}$–$C_{18}$)-alkanesulfonic acids and furthermore emulsifiers from the group comprising salts of ($C_{10}$–$C_{16}$)-alkyl-mono- to -hexaglycol ether-sulfates and salts of $\alpha$-($C_{14}$–$C_{19}$)-alkenol-sulfates. It is particularly favorable to use the salts of dodecylbenzenesulfonic acid. The term salts means alkali metal, alkaline earth metal or ammonium salts, in particular Na or Ca salts. The formulations according to the invention contain the anionic emulsifiers to the extent of 2–4% by weight, preferably 2.5–3.5% by weight.

Nonionic emulsifiers which can be used are: castor oil oxyethylates containing 9 to 40 mol of ethylene oxide (EO); ($C_{16}$–$C_{20}$)-alkanols which have been reacted with 1 to 15 mol of propylene oxide and then with 1 to 30 mol of ethylene oxide; polymerization products of propylene oxide and ethylene oxide containing 10 to 80% by weight of ethylene oxide and 20 to 90% by weight of propylene oxide; n-butanol-propylene oxide-ethylene oxide block oxyalkylate; xylenol oxyethylate containing 3 to 5 mol of ethylene oxide; ethoxylated ($C_8$–$C_{12}$)-alkylphenols or propoxylated and ethoxylated tributylphenols. The ethoxylated alkylphenols mentioned preferably contain 8 to 12 mol of ethylene oxide. Propoxylated and ethoxylated tributylphenols are to be understood, in particular, as meaning those which are obtained by reaction of tributylphenols with 8 to 12 mol of propylene oxide and then 1 to 30 mol of ethylene oxide. The n-butanol-propylene oxide-ethylene oxide block oxyalkylate can consist to the extent of 1–3% by weight of n-butanol, to the extent of 40–50% by weight of propylene oxide and to the extent of 50–60% by weight of ethylene oxide. It preferably consists of 2% by weight of n-butanol, 44% by weight of propylene oxide and to the extent of 54% by weight of ethylene oxide (Hoe S 3510, Hoechst AG).

The formulations according to the invention contain these nonionic emulsifiers to the extent of 4–10% by weight, in particular 6–8% by weight.

Mixtures of various anionic and nonionic emulsifiers can also be used according to the invention.

Particularly preferred combination partners for the salts of dodecylbenzenesulfonic acid are the n-butanol-propylene oxide-ethylene oxide block oxyalkylates (for example Hoe S 3510).

The alcohols (solvents) which can be used according to the invention are either short-chain ($C_2$–$C_3$)-alkanols or long-chain ($C_4$–$C_{16}$)-alkanols. ($C_4$–$C_{12}$)-alkanols, in particular n-hexanol, are preferably employed because of their higher boiling point and flash point. Mixtures of various alcohols also fulfil the purpose according to the invention. The finished formulations contain the alcohols to the extent of 2–20% by weight, in particular 4–15% by weight.

The combination of a calcium salt of dodecylbenzenesulfonic acid with an n-butanol-propylene oxide-ethylene oxide block oxyalkylate and n-hexanol is particularly preferred for the preparation of highly concentrated emulsifiable concentrates of compounds of the formula I (Ia).

The formulation auxiliaries mentioned are substances which are adequately known to the expert and which are described in the literature (cf. Winnacker-Küchler, "Chemische Technologie (Chemical Technology)", Volume 7, C. Hauser Verlag Munich, 4th Edition, 1986; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; and Schönfeldt, "Grenzflächenaktive Äthylenoxidaddukte (Surface-active ethylene oxide adducts)", Wiss. Verlagsgesell., Stuttgart 1976).

Examples of formulations according to the invention are summarized in the following Table II:

TABLE II

| Content of compound Ia % | Ca phenyl-sulfonate % 1) | Hoe S 3510 % 4) | Emul-sogen EL 9.5 % 5) | Solvent % | Spontaneous emulsifiability |
|---|---|---|---|---|---|
| 80.0 | 3.0 | 7.0 | | 10.0 n-butanol | 3 |
| 85.0 | 3.0 | 7.0 | | 5.0 n-butanol | 3–4 |
| 80.0 | 3.0 | 7.0 | | 10.0 isobutanol | 3 |
| 85.0 | 3.0 | 7.0 | | 5.0 isobutanol | 3 |
| 80.0 | 2.9 | 7.1 | | 10.0 2-ethylhexanol | 2–3 |
| 80.0 | 3.0 | 7.0 | | 10.0 n-pentanol | 2–3 |
| 80.0 | 3.0 | 7.0 | | 10.0 n-hexanol | 2 |
| 85.0 | 3.0 | 7.0 | | 5.0 n-hexanol | 2 |
| 80.0 | 3.3 | 7.0 | | 7.7 n-hexanol | 2–3 |
| 80.0 | 3.3 | 7.7 | | 9.0 n-hexanol | 2 |
| 80.0 | 2.8 | 6.6 | | 10.6 n-hexanol | 1–2 |
| 85.0 | 2.9 | 6.7 | | 5.4 n-hexanol | 1–2 |
| 82.0 | 2.9 | 6.7 | | 8.4 n-hexanol | 1 |
| 78.0 | 2.8 | 6.6 | | 12.6 n-hexanol | 1 |

The emulsifiable concentrates listed in Tables I and II were prepared by the customary method, i.e. by simple mixing of the starting components in a stirred flask (cf. Winnacker-Küchler, "Chemische Technologie (Chemical Technology)".

The invention is explained by the following preparation examples:

The individual components are mixed in a stirred flask.

I. 85.00% by weight of a compound of the formula I 3.00% by weight of Ca phenylsulfonate[1]) 7.00% by weight of Hoe S 3510[4]) 5.00% by weight of isobutanol The mixture is homogenized by stirring for about 1 hour. A clear solution is then obtained, which shows an adequate spontaneous emulsifiability in a 2% strength dilution in CIPAC standard water D (CIPAC Handbook Volume I (1970), page 878) of 30° C. (Rating FIG. 3)

II. 80.00% by weight of a compound of the formula I 2.90% by weight of Ca phenylsulfonate[1]) 7.10% by weight of Hoe S 3510[4]) 10.00% by weight of 2-ethylhexanol are homogenized as described under I until a clear solution is obtained. A good to adequate spontaneous emulsifiability is observed on preparation of a 5% strength spray liquor in CIPAC standard water D of 30° C. (Rating FIG. 2–3)

III. 82.00% by weight of a compound of the formula I 2.90% by weight of Ca phenylsulfonate[1]) 6.70% by weight of Hoe S 3510[4]) 8.40% by weight of n-hexanol are homogenized as described under I until a clear solution is obtained.

When used at 2 to 5% strength in CIPAC standard water D of 30° C., a very good spontaneous emulsifiability is found. (Rating FIG. 1)

I claim:

1. A highly concentrated emulsifiable concentrate of a compound of the formula I

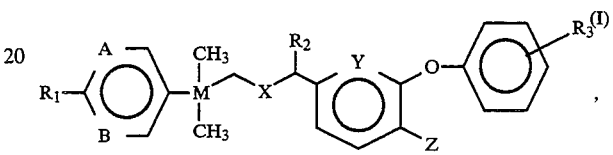

in which

A, B = independently of one another CH, $CR_4$ or N,

X = $CH_2$, O or S,

Y = CH or N,

Z = H or F, $R_1$ and $R_4$ = independently of one another H, halogen, $(C_1-C_3)$-alkyl, $(C_1-C_3)$-halogenoalkyl, $(C_1-C_3)$-alkoxy, $(C_1-C_3)$-halogenoalkoxy, $(C_1-C_4)$-alkylthio or $(C_1-C_4)$-halogenoalkylthio, or $R_1$ and $R_4$ together = —$CH_2$—O—$CH_2$—;

$R_2$ = H, $(C_1-C_3)$-alkyl, ethynyl, vinyl, halogen or cyano, $R_3$ = H, halogen, $(C_1-C_4)$-alkyl or $(C_1-C_3)$-alkoxy and M = C or Si, which contains a combination of an anionic and a nonionic emulsifier with a $(C_6-C_8)$-alkanol; wherein said concentrate contains 60 to 90% by weight of the compound of formula I and, wherein there is up to about 3% by weight of the anionic emulsifier, and there is up to about 7% by weight of the anionic emulsifier.

2. An emulsifiable concentrate as claimed in claim 1, in which, in formula I, A and B = CH or N, X = $CH_2$, $R_1$ = $(C_1-C_3)$-alkoxy, $R_2$ = H, $R_3$ = H or F and M = Si.

3. An emulsifiable concentrate as claimed in claim 1, in which, in formula I, M = Si, $R_1$ = ethoxy, A and B = CH, X = $CH_2$, $R_2$ = H, Y = CH, Z = F and $R_3$ = H.

4. An emulsifiable concentrate as claimed in claim 1, which contains 2–20% by weight of the alkanol.

5. An emulsifiable concentrate as claimed in claim 1, which contains 70–85% by weight of a compound of the formula I, and 4–15% by weight of the alkanol.

6. An emulsifiable concentrate as claimed in claim 1 in which an alkali metal or alkaline earth metal salt of dodecylbenzenesulfonic acid is used as the anionic emulsifier, and n-butanol-propylene oxide-ethylene oxide block oxyalkylate is used as the nonionic emulsifier and n-pentanol, n-hexanol or 2-ethylhexanol is used as the $(C_6-C_8)$-alkanol.

7. An emulsifiable concentrate as claimed in claim 1, in which n-hexanol is the $C_6$-alkanol.

8. A method of combating harmful insects or acarids, which comprises applying an active amount of an emulsifiable concentrate as claimed in claim 1 to these or to the plants, areas or substrates infested with these.

9. A method for combating harmful insects or acarids by applying to the locus thereof an emulsifiable concentrate, said emulsifiable concentrate being of a compound of the formula I

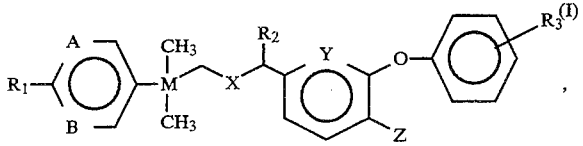

in which

A, B = independently of one another CH, $CR_4$ or N,
X = $CH_2$, O or S,
Y = CH, or N,
Z = H or F,
$R_1$ and $R_4$ = independently of one another H, halogen, ($C_1$-$C_3$)-alkyl, $C_1$-$C_3$-halogenoalkyl, ($C_1$-$C_3$)-alkoxy, ($C_1$-$C_3$)-halogenoalkoxy, ($C_1$-$C_4$)-alkylthio or ($C_1$-$C_4$)-halogenoalkylthio, or $R_1$ and $R_4$ together = —$CH_2$—O—$CH_2$—;
$R_2$ = H, ($C_1$-$C_3$)-alkyl, ethynyl, vinyl, halogen or cyano,
$R_3$ = H, halogen, ($C_1$-$C_4$)-alkyl or ($C_1$-$C_3$)-alkoxy and
M = C or Si, which contains a combination of an anionic and a nonionic emulsifier with a ($C_6$-$C_8$)-alkanol; wherein said concentrate contains 60 to 90% by weight of the compound of formula I and, wherein there is up to about 3% by weight of the anionic emulsifier, and there is up to about 7% by weight of the nonionic emulsifier; said method comprising applying an active amount of the emulsifiable concentrate to said insects or acarids, or to plants, areas or substrates infested with said insects or acarids.

10. A highly concentrated emulsifiable concentrate of a compound of the formula I

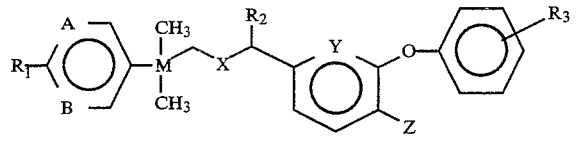

in which

A, B = independently of one another CH,
X = $CH_2$,
Y = CH,
Z = F,
$R_1$ = ethoxy,
$R_2$ = H,
$R_3$ = H, and
M = Si, which contains a combination of an anionic and a nonionic emulsifier with a ($C_6$-$C_8$)-alkanol; wherein said concentrate contains 60 to 90% by weight of the compound of formula I and, wherein there is up to about 3% by weight of the anionic emulsifier, and there is up to about 7% by weight of the nonionic emulsifier.

11. The highly concentrated emulsifiable concentrate of claim 10 wherein the ($C_6$-$C_8$)-alkanol is a $C_6$-alkanol.

12. The highly concentrated emulsifiable concentrate of claim 10 wherein the ($C_6$-$C_8$)-alkanol is a $C_8$-alkanol.

13. The highly concentrated emulsifiable concentrate of claim 11 wherein the $C_6$-alkanol is n-hexanol.

14. The highly concentrated emulsifiable concentrate of claim 12 wherein the $C_8$-alkanol is 2-ethylhexanol.

15. The method of claim 9 wherein:
A, B = independently of one another CH,
X = $CH_2$,
Y = CH,
Z = F,
$R_1$ = ethoxy,
$R_2$ = H,
$R_3$ = H, and
M = Si.

16. The method of claim 15 wherein the ($C_6$-$C_8$)-alkanol is a $C_6$-alkanol.

17. The method of claim 15 wherein the ($C_6$-$C_8$)-alkanol is a $C_8$-alkanol.

18. The method of claim 16 wherein the $C_6$-alkanol is n-hexanol.

19. The method of claim 17 wherein the $C_8$-alkanol is 2-ethylhexanol.

20. The highly concentrated emulsifiable concentrate of claim 1 wherein the ($C_6$-$C_8$)-alkanol is a $C_6$-alkanol.

21. The highly concentrated emulsifiable concentrate of claim 1 wherein the ($C_6$-$C_8$)-alkanol is a $C_8$-alkanol.

22. The highly concentrated emulsifiable concentrate of claim 21 wherein the $C_8$-alkanol is 2-ethylhexanol.

23. A method for combating harmful insects or acarids comprising
preparing a 2 to 5% strength dilution of the highly concentrated emulsifiable concentrate of claim 1; and
applying an active amount of the dilution to said insects or acarids, or to plants, areas or substances infested with said insects or acarids.

24. The emulsifiable concentrate as claimed in claim 6 wherein there is less than 3% by weight of the anionic emulsifier, and there is less than 7% by weight of the nonionic emulsifier.

25. The emulsifiable concentrate as claimed in claim 24 wherein the ($C_6$-$C_8$)-alkanol is n-hexanol.

26. The highly concentrated emulsifiable concentrate as claimed in claim 10 wherein an alkali metal or alkaline earth metal salt of dodecyl benzenesulfonic acid is used as the anionic emulsifier, n-butanol-propylene oxide-ethylene oxide block oxyalkylate is used as the nonionic emulsifier and, n-hexanol or 2-ethylhexanol is used as the ($C_6$-$C_8$)-alkanol.

27. The highly concentrated emulsifiable concentrate as claimed in claim 26 wherein there is less than 3% by weight of the anionic emulsifier and there is less than 7% by weight of the non-ionic emulsifier.

28. The highly concentrated emulsifiable concentrate as claimed in claim 27 wherein the ($C_6$-$C_8$)-alkanol is n-hexanol.

* * * * *